(12) United States Patent
Kang et al.

(10) Patent No.: US 9,121,850 B2
(45) Date of Patent: Sep. 1, 2015

(54) CARTRIDGE FOR DETECTING TARGET ANTIGEN AND METHOD FOR DETECTING TARGET ANTIGEN USING THE SAME

(75) Inventors: Da Yeon Kang, Seoul (KR); Sun Kil Kang, Seoul (KR); Tae Young Kim, Seoul (KR); Seung Mok Han, Seoul (KR); Kyu Ho Song, Seoul (KR); Guei Sam Lim, Seoul (KR); Ji Su Kim, Seoul (KR)

(73) Assignee: LG ELECTRONICS INC., Seoul (KR)

( * ) Notice: Subject to any disclaimer, the term of this patent is extended or adjusted under 35 U.S.C. 154(b) by 884 days.

(21) Appl. No.: 13/350,132

(22) Filed: Jan. 13, 2012

(65) Prior Publication Data

US 2012/0190130 A1   Jul. 26, 2012

(30) Foreign Application Priority Data

Jan. 20, 2011   (KR) .......................... 10-2011-0005719

(51) Int. Cl.
*G01N 33/566* (2006.01)
*G01N 33/543* (2006.01)
*G01N 21/64* (2006.01)
*G01N 21/65* (2006.01)

(52) U.S. Cl.
CPC ...... *G01N 33/54366* (2013.01); *G01N 21/6428* (2013.01); *G01N 21/65* (2013.01); *G01N 2458/10* (2013.01)

(58) Field of Classification Search
None
See application file for complete search history.

(56) References Cited

U.S. PATENT DOCUMENTS

2013/0265054 A1\* 10/2013 Lowery et al. ................ 324/319

\* cited by examiner

*Primary Examiner* — Ann Lam
(74) *Attorney, Agent, or Firm* — Birch, Stewart, Kolasch & Birch, LLP

(57) ABSTRACT

There are provided a cartridge for detecting a target antigen and a method for detecting a target antigen existing in a biological sample using the cartridge. In the cartridge, multiple detections of various antigens can be rapidly and conveniently performed, and a plurality of target antigens can be quantitatively analyzed using one cartridge, thereby reducing time and cost.

19 Claims, 2 Drawing Sheets

CARTRIDGE FOR DETECTING TARGET ANTIGEN AND METHOD FOR DETECTING TARGET ANTIGEN USING THE SAME

CROSS-REFERENCE TO RELATED APPLICATION

This application claims the benefit of Korean Patent Application No. 2011-0005719, filed 20, Jan. 2011, the disclosure of which is hereby incorporated herein by reference in its entirety.

BACKGROUND OF THE INVENTION

1. Field of the Invention

An aspect of the present invention relates to a cartridge for detecting a target antigen and a method for detecting a target antigen existing in a biological sample using the cartridge.

2. Description of the Related Art

Test methods for obtaining information on diseases by extracting patients' blood or body fluids are generalized, but much time and cost for the test methods is taken because the test methods should be performed in specialized agencies. Recently, in order to solve such problems, necessity of point-of-care analysis has been raised under the object of rapidity, precision and convenience. Accordingly, requirements of small measuring instruments are rapidly increased so that a doctor, nurse, clinical pathologist or patient can directly perform a test.

Many small measuring instruments such as an immune sensor and an enzyme sensor have been developed to analyze a specific substance. However, in order to measure a plurality of detection substances at the same time, different strips are used or it takes more time and cost than need be, due to the interference phenomenon between substances.

Accordingly, studies on point-of-care testing (POCT) capable of simultaneously measuring multiple components have been actively conducted so as to provide effective tests necessary for patients.

SUMMARY OF THE INVENTION

Embodiments of the present invention provide a cartridge for detecting a target antigen including a detection structure.

Embodiments of the present invention also provide a method for detecting a target antigen existing in a biological sample the cartridge for detecting the target antigen.

As the invention allows for various changes and numerous embodiments, particular embodiments will be illustrated in the drawings and described in detail in the written description. However, the present invention is not limited to the specific embodiments and should be construed as including all the changes, equivalents, and substitutions included in the spirit and scope of the present invention. In the following description, detailed explanation of known related functions and constitutions may be omitted to avoid unnecessarily obscuring the subject manner of the present invention.

Terms used in this application are used for just describing predetermined embodiments and not used for limiting the present invention. Expression of the singular number includes expression of the plural numbers if the singular number does not have a meaning different from the plural numbers. In this application, it will be appreciated that terms "include" or "have" are used for indicating that characteristics, numbers, steps, operations, constituent elements, components or combinations thereof are provided and existence or adding possibility of one or more different characteristics or numbers, steps, operations, constituent elements, components, and combinations thereof is not previously excluded.

Terms such as "first," "second," etc. may be used in describing various constituent elements, but the constituent elements should not be limited by the terms. The terms are used only for differentiate one constituent element from other constituent elements.

In this specification, the term "particle" refers a particle having a diameter is 1 to 1000 nm, and is preferably a nanoparticle. More preferably, the particle is a particle having a diameter of 10 to 1000 nm. Components of the particle may include, for example, metal such as gold, silver, copper, aluminum, nickel, palladium or platinum, a semiconductor material such as CdSe, CdS, InAs or InP, and an inert material such as polystyrene, latex, acrylate or polypeptide. However the present invention is not limited thereto.

In this specification, the term "detectable label" refers to an atom or molecule used to specifically detect a molecule including the label among the same type of molecules without the label. For example, the detectable label may include colored beads, an antigen determinant, an enzyme, a hybridizable nucleic acid, a chromophore material, a fluorescent material, a phosphorescent material, an electrically detectable material, a material providing modified fluorescence-polarization or modified light-diffusion, and/or a quantum dot. However, the present invention is not limited thereto. In addition, the detectable label may include a radioisotope such as $P^{32}$ or $S^{35}$, a chemiluminescent compound, a labeled binding protein, a heavy metal atom, a spectroscopic marker such as a dye, or a magnetic label. The dye may include, for example, a quinoline dye, a triarylmethane dye, a phthalein dye, an azo dye and a cyanine dye. However, the present invention is not limited thereto.

In this specification, the term "polynucleotide" refers to a polymer of ribonucleotides or deoxyribonucleotides, which can be single or double-stranded. The polynucleotide may include analogues of natural nucleotide as long as it is not particularly mentioned. The polynucleotide may include an oligonucleotide of which length is short.

In this specification, the term "specifically binding" or "specifically recognizing" is identical to that known by those skilled in the art, and refers to an immunological reaction through specific interaction between an antigen and an antibody. That is, a specific antigen is specifically bound to a specific antibody due to the peculiarity of antigen-antibody reaction.

In this specification, the term "substantially complementary sequence" refers to a sequence capable of hybridizing a first single-stranded polynucleotide and a second single-stranded nucleotide under stringent conditions known by those skilled in the art. The stringent conditions may be determined by controlling temperature, ion intensity (buffer solution concentration), existence of a compound such as an organic solvent, etc., and may be determined different depending on hybridized sequences. For example, the stringent conditions may be a condition under which the first single-stranded polynucleotide and the second single-stranded polynucleotide are cleansed at a temperature of 50° C. using 0.015M sodium chloride/0.0015M sodium citrate/0.1% sodium dodecyl sulfate or a condition under which the first single-stranded polynucleotide and the second single-stranded polynucleotide are hybridized at a temperature of 55° C. in a hybridizing buffer solution (including 50% formamide, 2×SSC and 10% dextran sulfate) and then cleansed at the temperature of 55° C. using EDTA-contained 0.1×SSC.

According to an aspect of the present invention, there is provided a cartridge for detecting a target antigen, the cartridge including: a first channel configured to include a detection structure included in an inside thereof and have a sample injection part, wherein the detection structure is composed of a first single-stranded polynucleotide to which a particle is connected and a second single-stranded polynucleotide to which a first antibody is connected, and a double-stranded polynucleotide is formed by binding at least parts of the first and second single-stranded polynucleotides to each other; a reaction part configured to be connected to the first channel so that a fluid is communicated between the reaction part and the first channel, wherein a second antibody is fixed to an internal surface of the reaction part; and a second channel configured to be connected to the reaction part so that a fluid is communicated between the second channel and the reaction part.

That is, the cartridge includes a first channel, a reaction part and a second channel. The first channel includes a detection structure in an inside thereof and has a sample injection part. The detection structure is composed of a first single-stranded polynucleotide and a second single-stranded polynucleotide. The reaction part is connected to the first channel so as to a fluid is communicated between the reaction part and the first channel, and a second antibody is fixed to an internal surface of the reaction part. The second channel is connected to the reaction part so that a fluid is communicated between the second channel and the reaction part.

According to one embodiment, the detection structure may include a first single-stranded polynucleotide to which a particle is connected.

The particle may be a nanoparticle, and the particle may be connected to the 5' end or 3' end of the first single-stranded polynucleotide. The connection may be formed by chemically binding the first single-stranded polynucleotide to the particle. The first single-stranded polynucleotide may introduce a reactive group to an end thereof, and may be fixed to the particle through the reactive group. Here, the reactive group may be selected from the group consisting of aldehyde, carboxyl, ester, activated ester, amino and combinations thereof. Alternatively, the first single-stranded polynucleotide having no reactive group may be fixed to a surface of the particle by coating the reactive group on the surface of the particle, or the first single-stranded polynucleotide may be fixed to the surface of the particle by introducing the reactive group to both the first single-stranded polynucleotide and the surface of the particle.

One or more detectable labels may be bound to the particle or the first single-stranded polynucleotide, and the number of detectable labels to be bound to the particle or the first single-stranded polynucleotide may be determined depending on the size of the nanoparticle. That is, the particle or the first single-stranded polynucleotide further may include a detectable label radiating a signal selected from the group consisting of a magnetic signal, an electrical signal, a light emitting signal such as fluorescence or Raman, a scattered light signal and a radioactive signal.

According to one embodiment, the detection structure may include a second single-stranded polynucleotide to which a first antibody is connected.

The first antibody may be specifically bound to a target antigen, and the first antibody may be connected to the 3' end or 5' end of the second single-stranded polynucleotide. The first antibody used for the detection structure of the present invention has different kinds depending on the kind of the target antigen to be detected.

In the detection structure of the present invention, the particle may be connected to one end of the first single-stranded polynucleotide, and the first antibody may be connected to the other end of the second single-stranded polynucleotide. That is, the particle may be connected to one side of the detection structure, and the first antibody may be connected to the other side of the detection structure. If the particle and the first antibody are positioned at the same side of the detection structure, the particle may interfere with the binding between the first antibody and the target antigen, which is not preferable.

According to the present invention, a double-stranded polynucleotide may be formed by binding at least parts of the first and second single-stranded polynucleotides to each other. To this end, the first single-stranded polynucleotide may include a substantially complementary sequence in the second single-stranded polynucleotide. That is, a part of a consecutive sequence included in the first and second single-stranded polynucleotides may include a substantially complementary sequence so as to form the double-stranded polynucleotide. Here, the complementary sequence of the second single-stranded polynucleotide in the first single-stranded polynucleotide may include not only a perfectly complementary sequence but also a substantially complementary sequence.

According to one embodiment, the first channel may include one or more kinds of detection structures, and the detection structure may include one or more kinds of first antibodies recognizing different target antigens. The first and second antibodies may include two or more kinds of antibodies specifically bound to different target antigens, and the first channel may include two or more kinds of detection structures different first antibodies. That is, the detection structure may be prepared by changing the kind of first antibody depending on the kind of target antigen. For example, if it is intended to prepare a cartridge capable of detecting five kinds of target antigens, five kinds of first antibodies may also be prepared, and the five kinds of first antibodies may be specifically bound to the five kinds of target antigens, respectively.

According to one embodiment, the substantially complementary sequence may have, for example, a length of 10 to 100 bp. Each of the first and second single-stranded polynucleotides may have a length identical to each other or lengths different from each other. That is, the two or more kinds of detection structures may include the first and second single-stranded polynucleotides having different lengths. Particularly, the detection structures may be prepared to have different lengths of the substantially complementary sequence in the first and second single-stranded polynucleotides depending on the kind of target antigen to be detected. For example, three kinds of detection structures may be prepared to have substantially complementary sequences of 10, 20 and 30 bp in the first and second single-stranded polynucleotides.

According to one embodiment, the two or more kinds of detection structures may include the first and second signal-stranded polynucleotides having different contents of guanine and cytosine.

The degree of modification of the polynucleotide is changed depending on its length and/or content of guanine and cytosine. Hence, in the present invention, it is possible to detect two or more antigens using a time difference depending on the degree of modification.

According to one embodiment, the sample injection part is preferably formed at one end of the first channel. More preferably, the sample injection part is formed so that the one end of the first channel is opened.

The reaction part may be connected to the other end of the first channel, opposite to the sample injection part, and the second channel may be connected to the other end of the reaction part, opposite to the first channel. This is because it is preferable in terms of the mobility and safety of a target antigen and a complex body to which the target antigen is bound.

According to one embodiment, a detection part capable of detecting a signal generated from the particle may be further included in the reaction part and/or the second channel.

According to another aspect of the present invention, there is provided a method for detecting a target antigen, the method including: injecting a biological sample containing a target antigen into the sample injection part of the cartridge so that the target antigen is contacted with a detection structure; contacting the detection structure bound to the target antigen with a second antibody of the reaction part; separating a particle from the detection structure by applying heat to the reaction part; and detecting the separated particle.

In the present invention, the method may be used to detect a target antigen in a capture-ELISA method. The capture-ELISA method generally includes coating a capturing antibody on a surface of a solid substrate; allowing the capturing antibody to react with a sample (e.g., a sample including a target antigen); allowing a resultant obtained through the reaction to react with a detecting antigen bound to a detectable label generating a signal and specifically reacting with the target antigen; and measuring the signal generated from the detectable label.

In the present invention, the antibody (i.e., capturing antibody) specifically bound to one or more kinds of target antigens to be detected may be fixed to the reaction part of the cartridge, depending on the antigen to be detected.

Operations of the method will be described in detail as follows.

The method may include injecting a biological sample containing a target antigen into the sample injection part of the cartridge so that the target antigen is contacted with a detection structure.

The biological sample applicable to the method may be, for example, whole blood, blood plasma, serum, tear, sputum, urine, snivel or body fluid of a person or animal, but the present invention is not limited thereto. The biological sample may be injected into the sample injection part by being diluted in a reactive solution such as a buffering solution depending on the kind of biological sample. The target antigen in the biological sample injected into the sample injection part is specifically bound to a detection structure in the first channel, particularly a first antibody of the detection structure.

The presence of pathogenic organs and antibodies of hepatitis C, hepatitis B, influenza virus, bird flu virus, Rotavirus, AIDS, syphilis, *Chlamydia*, malaria, typhoid fever, stomach ulcer, tuberculosis, SARS, dengue, leprosy, etc. may be tested from the biological sample. The biological sample may be used to identify the presence of pregnant, ovulation, cancer marker, heart disease marker, etc. The biological sample may be used to identify, from food, the presence of *salmonella, vibrio, campylobacter*, Enterohamorrhagic *Escherichia coli* (EHEC), *yersinia*, etc. As such, the biological sample can be applied to tests and analyses in various fields.

Then, the method may include contacting the detection structure bound to the target antigen with a second antibody of the reaction part.

The complex body of the target antigen and the detection structure, formed in the first channel of the cartridge, may be moved to the reaction part connected to the first channel so that a fluid is communicated between the reaction part and the first channel. The target antigen in the complex body of the target antigen and the detection structure may be contacted with the second antibody fixed to an internal surface of the reaction part.

Then, the method may include separating a particle from the detection structure by applying heat to the reaction part, and detecting the separated particle. The separating of the particle from the detection structure may separate the first single-stranded polynucleotide connected to the particle from the detection structure.

According to one embodiment, the method may further include cleansing the detection structure not bound to the target antigen by injecting a cleansing solution into the reaction part before the separating of the particle from the detection structure. Subsequently, if heat is applied to the reaction part, the first single-stranded polynucleotide formed with a double strand in the components constituting the detection structure is separated into single strands by the modification of the second single-stranded polynucleotide in the complex of the target antigen and the diction structure, specifically bound to the second antibody. Since the second single-stranded polynucleotide is connected to the first antibody, the second single-stranded polynucleotide is in a state in which the second single-stranded polynucleotide is bound to the target antigen. Since the first single-stranded polynucleotide is connected to the particle, the first single-stranded polynucleotide is in a state in which the first single-stranded polynucleotide is separated from the target antigen. Thus, the particle connected to the separated first single-stranded polynucleotide can be moved to the second channel connected to the reaction part so that a fluid is communicated between the second channel and the reaction part, and the separated particle can be detected in the second channel. The detecting of the separated particle may detect a quantity of the particle two times or more at a predetermined time interval.

According to one embodiment, the detected signal may be a signal selected from the group consisting of a magnetic signal, an electrical signal, a light emitting signal such as fluorescence or Raman, a scattered light signal and a radioactive signal. The identification of the detected signal means that the signal generated from the particle is measured in the detection part. Thus, it is possible to analyze the presence of the target antigen and the kind and quantity of antigen included in the biological sample.

BRIEF DESCRIPTION OF THE DRAWINGS

These and/or other aspects and advantages of the invention will become apparent and more readily appreciated from the following description of the embodiments, taken in conjunction with the accompanying drawings of which.

DETAILED DESCRIPTION OF THE INVENTION

The present invention is described more fully hereinafter with reference to the accompanying drawings, in which embodiments of the present invention are shown. This present invention may, however, be embodied in many different forms and should not be construed as limited to the embodiments set forth herein. Rather, these embodiments are provided so that this disclosure is thorough, and will fully convey the scope of the present invention to those skilled in the art.

Figure 1:
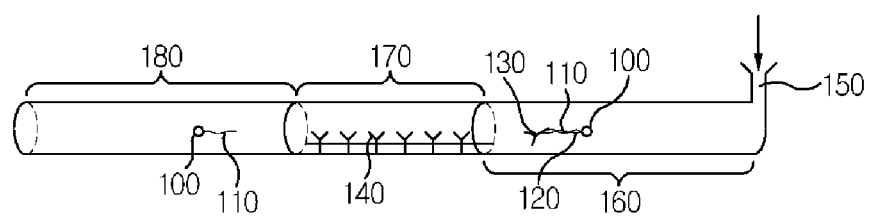
FIG. 1 is a schematic view showing a structure of a cartridge for detecting a target antigen according to an embodiment of the present invention.
Figure 2:
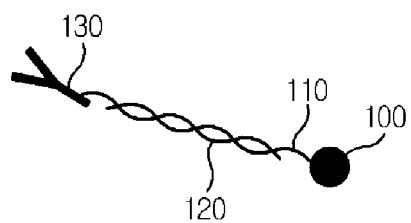
FIG. 2 is a schematic view showing a detection structure according to the embodiment of the present invention.
Figure 3:
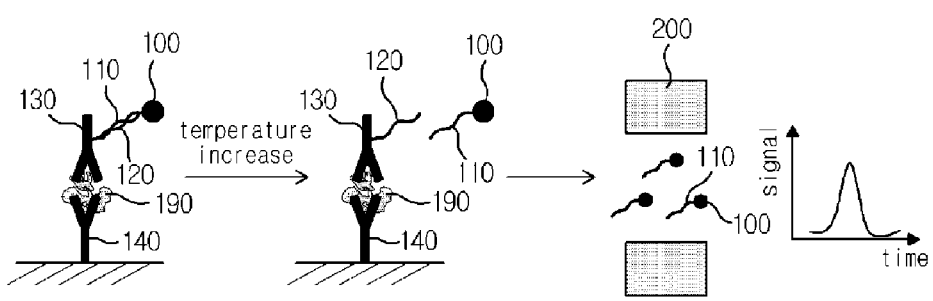
FIG. 3 is a schematic view illustrating a method for detecting a target antigen using the cartridge according to the embodiment of the present invention.
Figure 4:
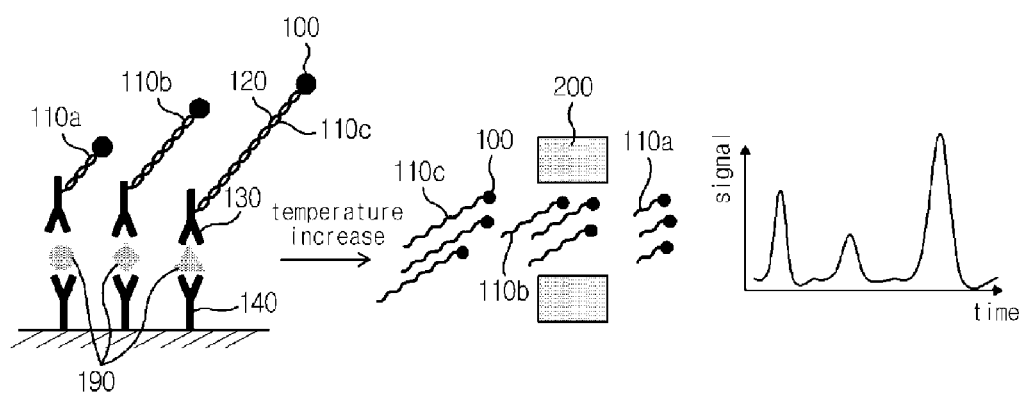
FIG. 4 is a schematic view illustrating a method for detecting various kinds of target antigens using the cartridge according to the embodiment of the present invention.

FIG. 1 is a schematic view showing a structure of a cartridge for detecting a target antigen according to an embodiment of the present invention. FIG. 2 is a schematic view showing a detection structure according to the embodiment of the present invention. FIGS. 3 and 4 illustrate a method for detecting one or various kinds of target antigens using the cartridge according to the embodiment of the present invention.

Hereinafter, a method for detecting a target antigen included in a biological sample using a cartridge for detecting a target antigen according to an embodiment of the present invention will be described in detail with reference to FIGS. 1 to 4.

FIG. 1 is an entire schematic view of a cartridge for detecting a target antigen. The outside of the cartridge is configured to include a sample injection part 150, a first channel 160, a reaction part 170 and a second channel 180. As shown in FIG. 2, a detection structure composed of a nanoparticle 100, a first single-stranded polynucleotide 110, a second single-stranded polynucleotide 120 and a first target antibody 130 is included in the inside of the first channel 160. A second antibody 140 fixed to an internal surface of the reaction part 170 is included in the reaction part 170.

For example, if a blood sample is injected into the sample injection part 160 so as to detect a target antigen existing in blood of a patient, the target antigen existing in the blood sample is moved to the reaction part 170 along the first channel 160 by reacting with a detection structure existing in the first channel 160. The complex body of the detection structure and the target antigen, moved to the reaction part 170, reacts with the second antibody 140 fixed to the internal surface of the reaction part 170. Then, if a cleansing solution is provided to the reaction part 170, only the complex body formed through antigen-antibody reaction remains, and the non-reactive material is washed out. Subsequently, the detection structure is modified by applying heat to the reaction part 170 so that a double-stranded polynucleotide of the detection structure is modified (so that the heat reaches a temperature more than Tm of the double-stranded polynucleotide). While the first single-stranded polynucleotide 110 and the second single-stranded polynucleotide 120 in the detection structure are modified, the nanoparticle 100 connected to the first single-stranded polynucleotide 110 is separated from the reaction part 170 and then moved to the second channel 180. Through the process described above, the target antigen in the biological sample can be separated at high resolution.

FIGS. 3 and 4 illustrate a method for detecting one or various kinds of target antigens included in a biological sample using the cartridge described above. Particularly, a phenomenon occurring in the reaction part 170 and the second channel 180 will be described in detail.

If the reaction part 170 is heated after the reaction is completed in the reaction part 170, the double strand of the first single-stranded polynucleotide 110 and the second single-stranded polynucleotide 120, included in the detection structure, is separated into single strands. Since the nanoparticle 100 is bound to an end of the separated first single-stranded polynucleotide 110, the nanoparticle 100 can be moved to the second channel 180. The quantity of the first antibody 130 bound to the target antigen in the reaction part 170 can be quantitatively analyzed by analyzing, through a detection part 200, the absorbance and fluorescent signal of the nanoparticle 100 having the first single-stranded polynucleotide 110 connected thereto, which is moved to the second channel 180. The method can easily detect a specific antigen even when a small quantity of the specific antigen is included in a blood sample.

The modification of the polynucleotide is shown at different temperatures depending on the concentration of salt near the polynucleotide or the content of guanine and cytosine in sequences constituting the polynucleotide. That is, if the concentration of the salt or the content of the guanine and cytosine in the polynucleotide is increased, the modification temperature is increased. The property is very effective in analyzing a plurality of materials at the same time. FIG. 4 illustrates a principle of simultaneously measuring a plurality of target antigens using the property.

In order to measure a plurality of target antigens 190, the detection structure including the first antigen 130, which can be specifically bound to each of the target antigens 190, may be variously prepared. If polynucleotides have different lengths are used in each of the detection structures, the plurality of target antigens 190 can be analyzed through one detection process. For example, as illustrated in FIG. 4, three detection structures are prepared so as to analyze three target antigens 190, and first single-stranded polynucleotides 110a, 110b and 110c having different lengths and second single-stranded polynucleotides can be connected to nanoparticles 100 and first antibodies 130, respectively. Although various kinds of second antibodies 140 capable of being specifically bound to the respective target antigens 190 are fixed to the internal surface of the reaction part 170, each of the antibodies 140 reacts with a corresponding target antigen to which the antibody 140 can be specifically bound in the various target antigens due to the peculiarity of antigen-antibody reaction. In addition, the second single-stranded polynucleotide 120 connected to each of the first antibodies 130, the first single-stranded polynucleotide 110 complementarily bound to the second single-stranded polynucleotide 120 and the nanoparticle 100 connected thereto can also be bound to the target antigen 190. In this case, it is assumed that parts complementarily bound between the first single-stranded polynucleotides 110a, 110b and 110c and the second single-stranded polynucleotides in 120 in each of the detection structures prepared so as to recognize the different target antigens 190 include 12, 24 and 36 bases, respectively. When heat is applied to the reaction part 170, the complementarily bound polynucleotides are sequentially modified into single strands according to the number of bases, and sequentially moved to the second channel 180. Since the nanoparticles 100 can be sequentially analyzed at a time interval in the detection part 200 existing in the second channel 180, the analysis corresponding to each of the target antigens 190 can be quantitatively performed.

In the cartridge for detecting a target antigen according to the present invention, multiple detections of various antigens can be rapidly and conveniently performed, and a plurality of target antigens can be quantitatively analyzed using one cartridge, thereby reducing time and cost.

Although the present invention has been described in connection with the preferred embodiments, the embodiments of the present invention are only for illustrative purposes and should not be construed as limiting the scope of the present invention. It will be understood by those skilled in the art that various changes and modifications can be made thereto within the technical spirit and scope defined by the appended claims.

What is claimed is:

1. A cartridge for detecting a target antigen, the cartridge comprising:
    a first channel configured to comprise a detection structure included in an inside thereof and have a sample injection part, wherein the detection structure is composed of a first single-stranded polynucleotide to which a particle is connected and a second single-stranded polynucleotide to which a first antibody is connected, and a double-stranded polynucleotide is formed by binding at least parts of the first and second single-stranded polynucleotides to each other;
    a reaction part configured to be connected to the first channel so that a fluid is communicated between the reaction part and the first channel, wherein a second antibody is fixed to an internal surface of the reaction part; and
    a second channel configured to be connected to the reaction part so that a fluid is communicated between the second channel and the reaction part.

2. The cartridge of claim 1, wherein the particle is a nanoparticle.

3. The cartridge of claim 1, wherein the particle has a diameter of 10 to 1000 nm.

4. The cartridge of claim 1, wherein the first antibody is specifically bound to a target antigen.

5. The cartridge of claim 1, wherein, in the detection structure, the particle is connected to one end of the first single-stranded polynucleotide, and the first antibody is connected to the other end of the second single-stranded polynucleotide.

6. The cartridge of claim 1, wherein the particle is connected to the 5' end or 3' end of the first single-stranded polynucleotide, and the first antibody is connected to the 3' end or 5' end of the second single-stranded polynucleotide.

7. The cartridge of claim 1, wherein a part of a consecutive sequence included in the first and second single-stranded polynucleotides comprises a substantially complementary sequence so as to form the double-stranded polynucleotide.

8. The cartridge of claim 7, wherein the substantially complementary sequence has a length of 10 to 100 bp.

9. The cartridge of claim 1, wherein the sample injection part is formed at one end of the first channel.

10. The cartridge of claim 1, wherein the sample injection part is formed so that the one end of the first channel is opened.

11. The cartridge of claim 1, wherein the reaction part is connected to the other end of the first channel, opposite to the sample injection part.

12. The cartridge of claim 1, wherein the first and second antibodies comprise two or more kinds of antibodies specifically bound to different target antigens, and the first channel comprises two or more kinds of detection structures having different first antigens.

13. The cartridge of claim 1, wherein the two or more kinds of detection structures comprise first single-stranded polynucleotides having different lengths.

14. The cartridge of claim 1, wherein the two or more kinds of detection structures comprise first single-stranded polynucleotides having different contents of guanine and cytosine.

15. The cartridge of claim 1, wherein the second channel is connected to the other end of the reaction part, opposite to the first channel.

16. The cartridge of claim 1, wherein the particle or the first single-stranded polynucleotide further comprises a detectable label radiating a signal selected from the group consisting of a magnetic signal, an electrical signal, a light emitting signal such as fluorescence or Raman, a scattered light signal and a radioactive signal.

17. A method for detecting a target antigen, the method comprising:
    injecting a biological sample containing a target antigen into the sample injection part of the cartridge of claim 1 so that the target antigen is contacted with a detection structure;
    contacting the detection structure bound to the target antigen with a second antibody of the reaction part;
    separating a particle from the detection structure by applying heat to the reaction part; and
    detecting the separated particle.

18. The method of claim 17, wherein the separating of the particle from the detection structure separates a first single-stranded polynucleotide connected to the particle from the detection structure.

19. The method of claim 17, wherein the detecting of the separated particle detects a quantity of the particle two times or more at a predetermined time interval.

* * * * *